United States Patent
Shenk et al.

(10) Patent No.: US 9,212,349 B2
(45) Date of Patent: Dec. 15, 2015

(54) METHOD TO PRODUCE VIRUS IN CULTURED CELLS

(75) Inventors: Thomas Shenk, Princeton, NJ (US);
Emre Koyuncu, Princeton, NJ (US);
Joshua D. Rabinowitz, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 14/112,824

(22) PCT Filed: Apr. 18, 2012

(86) PCT No.: PCT/US2012/034040
§ 371 (c)(1),
(2), (4) Date: Dec. 30, 2013

(87) PCT Pub. No.: WO2012/145375
PCT Pub. Date: Oct. 26, 2012

(65) Prior Publication Data
US 2014/0113353 A1 Apr. 24, 2014

Related U.S. Application Data

(60) Provisional application No. 61/476,497, filed on Apr. 18, 2011.

(51) Int. Cl.
*C12N 7/00* (2006.01)

(52) U.S. Cl.
CPC .......... *C12N 7/00* (2013.01); *C12N 2710/16151* (2013.01); *C12N 2710/16751* (2013.01)

(58) Field of Classification Search
CPC ........... C12N 2710/16151; C12N 2710/16751; C12N 7/00
See application file for complete search history.

(56) References Cited

U.S. PATENT DOCUMENTS

| 5,360,736 A | 11/1994 | Provost et al. |
| 2009/0081251 A1 | 3/2009 | Mehtali et al. |
| 2010/0184190 A1 | 7/2010 | Truong-Le |

FOREIGN PATENT DOCUMENTS

WO  WO 2008/051698  *  5/2008  ............... C12N 7/08

OTHER PUBLICATIONS

Stoll et al (In Vitro 20:732-738, 1984).*
Horn et al (Journal of Animal Sciences 88:3128-3135, 2010).*
Kohn et al (Antimicrobial Agents and Chemotherapy 18:962-968, 1980).*
Horowitz et al (Vox Sanguinis 54:14-20 1988, abstract only).*
Koch et al (Acta Microbiologica Academiae Scientiarum Hungaricae 15:77-85, 1968).*
Makino et al (Journal of Virology 15:575-525, 1975).*
Pottathil et al (Journal of Biological Chemistry 260:5265-5270, 1985 and supplemental data).*
"11905—Chemically Defined Lipid Concentrate" [retrieved on Dec. 19, 2014] Retrieved from the Internet: <URL: http://www.lifetechnologies.com/us/en/home/technical-resources/media-formulation.249.htm>.*
Harper et al., High-titre, cryostable cell-free varicella zoster virus, *Arch. Virol.*, 143:1163-70 (1998).
Munger et al., Systems-level metabolic flux profiling identifies fatty acid synthesis as a target for antiviral therapy, *Nat. Biotech.*, 26:1179-86 (2008).
Munger et al., Dynamics of the cellular metabolome during human cytomegalovirus infection, *PLoS Pathog.*, 2:e132 (2006).
International Preliminary Report on Patentability, PCT/US2012/34040, dated Oct. 22, 2013.
International Search Report and Written Opinion of the International Searching Authority, United States Patent Authority, PCT/IS2012/34040, dated Aug. 3, 2012.

* cited by examiner

*Primary Examiner* — Mary E Mosher
(74) *Attorney, Agent, or Firm* — Marshall, Gerstein & Borun LLP

(57) ABSTRACT

A method for improving virus production in a host cell infected with the virus is provided.

10 Claims, 9 Drawing Sheets

METHOD TO PRODUCE VIRUS IN CULTURED CELLS

CROSS-REFERENCE TO RELATED APPLICATION

This application claims priority of U.S. provisional patent application No. 61/476,497 filed Apr. 18, 2011, the disclosure of which is incorporated in its entirely herein.

STATEMENT OF GOVERNMENT INTEREST

This invention was made with government support under Grant No. AI078063 and Grant No. CA082396 awarded by the National Institutes of Health. The government has certain rights in the invention.

FIELD OF THE INVENTION

The present disclosure relates to processes for virus production.

BACKGROUND

Since the ability to obtain adequate viral yields can limit vaccine manufacturing, improved methods of virus production are always needed to meet an important industrial and medical need. Previous work (Munger et al., *PLoS Pathog* 2:e132, 2006; Munger et al., *Nat Biotech* 26:1179-86, 2008)) has demonstrated that human cytomegalovirus (HCMV) induces the synthesis of fatty acids, and, importantly, that the virus requires the de novo synthesis of fatty acids to generate an optimal yield of infectious progeny. Despite this understanding, U.S. Pat. No. 5,360,736 discloses that that addition of lipids during growth of certain viruses, and in particular after initiation of infection of the cultured cells, inhibits virus production.

Preparation of stock virus is necessary for development of therapeutic methods and materials. Accordingly, improved methods for virus production are useful for improving virus yield, and more specifically for vaccine production.

DESCRIPTION OF THE INVENTION

Figure 1:
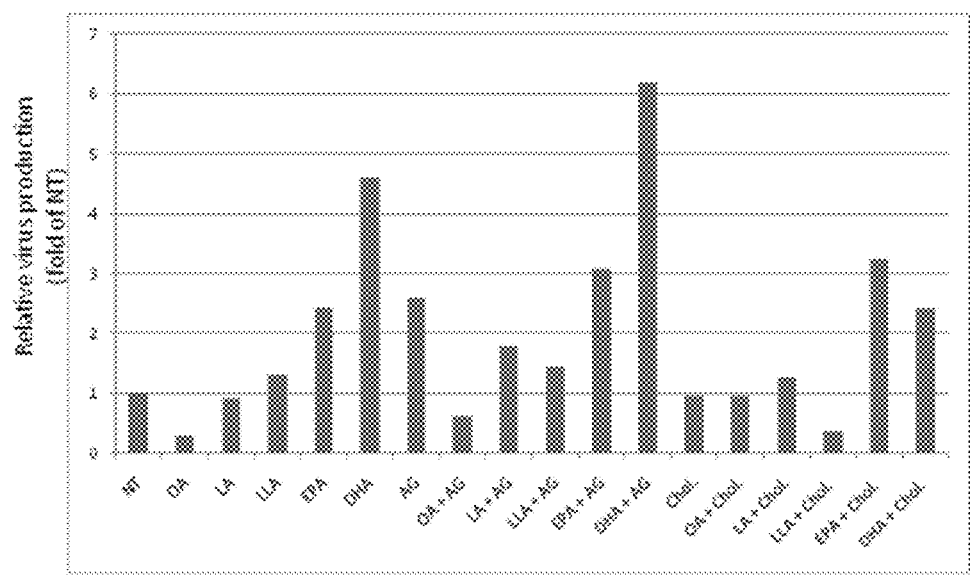
FIG. 1. The effect of different fatty acids as medium supplement on HCMV yields.

Provided herein is a method for increasing the yield of virus production from cultured cells. In general, a method is provided wherein supplementation of growth medium with a fatty acid increases the yield of viruses produced in infected cells in culture compared to the same method carried out in the absence of the fatty acid. In view of the art, the method provides an unexpected improvement on methods routinely practiced. The method provided is useful in combination with routinely utilized variables relating to conditions of cell growth and cell maintenance, both prior to infection and after virus infection of the cells in culture, and in combination with known methods of harvesting, preparing, stabilizing and storing virus stocks, that are described in U.S. Pat. No. 5,360,736, incorporated herein in its entirety for all that it discloses, and/or known to those skilled in the art of virus propagation and preparation of virus stocks.

In a general embodiment, a method is provided for virus production wherein an infected host cell is cultured in the presence of a fatty acid in amount and for a time appropriate to allow virus production. The method provides increased virus production compared to the same method performed in the absence of the fatty acid.

Accordingly, a method is provided for producing a virus comprising the step of culturing a host cell infected with a virus under conditions and for a time appropriate for producing the virus, wherein the conditions include a fatty acid in an amount and for a time effective to permit virus production. Production of virus is measured, in various aspects, by (i) the number of infectious virus particles, (ii) the number of virus particles, infectious and non-infectious, (iii) an amount of a specific viral antigen, and/or (iv) combinations of (i)-(iii). The method increases virus yield compared to the same method under conditions that do not include a fatty acid. In various aspects of the method, the conditions include the presence of a fatty acid and cholesterol. In various aspects of the method, the conditions further include a scavenging compound. In various aspects, the method is carried out under conditions which include no more than one fatty acid, no more than two fatty acids, no more than three fatty acids or no more than four fatty acids. In various aspects of the method, the conditions include at least two different fatty acids, at least three different fatty acids, at least four different fatty acids or four or more different fatty acids. In various aspects, the fatty acid or fatty acids is/are essentially homogeneous. An "essentially homogeneous" fatty is defined that includes about 5% or less contaminating fatty acids. For example and only for purposes of explanation, an essentially homogeneous fatty acid X include about 5% or less non-fatty acid X, wherein non-fatty acid X is a fatty acid that is not fatty acid X.

The method provided, in various aspects, further comprises the step of isolating said virus from medium of cell growth. In various aspects, the method further comprises the step of isolating the virus from the host cell. In various aspects, the method further comprises the step of infecting the host cells with the virus. In various aspect, the host cell is infected with a virus at different multiplicities of infection at a multiplicity of infection (MOI) of between about 1:25 and 1.625, of about 1:25, of about 1:125 or higher, or of between about 1:7 and 1:625. The method provided, in various aspects, further comprises the step of growing the host cells to confluence, to about 90%, about 80% confluence, about 70% confluence, about 60% confluence, about 50% confluence, or less than 50% confluence prior to infecting the host cells with the virus. The method in various aspects, further comprises the step of culturing the host cells after infecting the host cells with the virus. In various aspects, the method further comprises the step of adding or changing medium of growth for the host cells prior to isolating the virus. In various aspects, the method further comprises the step of incubating the host cells with an infecting virus for an adsorption period. In various aspects, the method further comprises the step of introducing the fatty acid, cholesterol and/or scavenging compound during the step of adding or changing the medium. The method, in various aspects, further comprises the step of introducing the fatty acid, cholesterol and/or scavenging compound prior to infecting the host cell with the virus, and/or introducing the fatty acid, cholesterol and/or scavenging compound after infecting the host cell with the virus. In various aspects, the method further comprises the step of introducing the fatty acid, cholesterol and/or scavenging compound at more than one time during the step of culturing the cells. An advantage of such repeated administration is the ability to maintain the desirable levels of the yield-enhancing components without reaching toxic levels at any point in the process, and the ability to tailor the levels of such yield-enhancing compounds to the specific demands of different stages of viral replication. In various aspects, the method further comprises the step of freezing the host cells prior to isolating the virus. In various aspects, the method further comprises the step isolating the virus without freezing the host cells. In various aspects, the method further comprises the step of sonicating the host cells to isolate the virus.

The method, in various aspects, further comprises the step freezing the host cells prior to isolating the virus. In various aspects, the method further comprises the step isolating the virus without freezing the host cells. In various aspects, method further comprises the step of sonicating the host cells to isolate the virus.

In various aspects, the method utilizes a host cell that is infection-susceptible to the virus, a host cell that is mammalian, a host cell is human, a host cell that is a fibroblast cell, or a host cell that is an MRC5 cell. In various aspects, the method utilizes a host cell that is an epithelial cell, a host cell that is a retinal cell, or a host cell that is an ARPE-19 cell. Those of ordinary skill in the art will readily appreciate that a large number of different cell types are amenable to use in the method and are contemplated by the disclosure.

In various aspects, the method is used with (and to produce) an enveloped DNA virus, a herpes virus, an alpha family herpes virus, a beta family herpes virus, a gamma family herpes virus, varicella zoster virus (VZV), cytomegalovirus (CMV), a pox virus, a non-enveloped picorna virus, including for example, but not limited to poliovirus, rhinovirus, hepatitis A virus, or foot and mouth disease virus, an RNA virus, influenza virus, herpes simplex virus, Epstein Barr virus, hepatitis C virus, Dengue virus, HIV, mumps virus, measles virus, rotavirus and/or parainfluenza virus.

In various aspects, the method utilizes cholesterol which is a cholesterol derivative or a cholesterol ester.

The method, in various aspects, utilizes a fatty acid which is a long chain fatty acid or a very long chain fatty acid, an omega-3 fatty acid, an omega-6 fatty acid, a naturally-occurring fatty acid, a derivative of a naturallyoccurring fatty acid, a non-naturally-occurring fatty acid, a free fatty acid, a fatty acid ester, a fatty acid derivative, a triglyceride, a diglyceride, a monoglyceride, a phopspholipid, a fatty acid that has at least 18 carbon, a fatty acid that has at least 20 carbons, a fatty acid that has at least 22 carbons, a fatty acid has at least 24 carbons, a fatty acid that has at least 26 carbon, a fatty acid that has at least 28 carbons, a fatty acid that has at least 30 carbons, a fatty acid has at least 32 carbons, a fatty acid that has at least 34 carbon, a fatty acid that has at least 36 carbons, a fatty acid that has at least 38 carbons, a fatty acid has at least 40 carbons, a fatty acid that is saturated, a fatty acid that is unsaturated, a fatty acid that is polyunsaturated, a fatty acid that has 1 or more double bonds, a fatty acid that has 2 or more double bonds, a fatty acid that has 3 and/or more double bonds, a fatty acid that has 4 or more double bonds, a fatty acid that has 5 or more double bonds, a fatty acid that has 6 and/or more double bonds, a fatty acid that has 7 or more double bonds, a fatty acid that has 8 or more double bonds, a fatty acid that has 9 or more double bonds, a fatty acid that has 10 or more double bonds, a fatty acid that has 11 or more double bonds, or a fatty acid that has 12 or more double bonds. In various aspects, the fatty acid is selected from the group consisting of oleic acid (OA), linoleic acid (LA), α-linolenic acid (LLA), eicosapentaenoic acid (EPA), docosahexaenoic acid (DHA), arachidonic acid (AA), hexacosanoic acid (HSA), octacosanoic acid (OSA), α-linolenic acid and/or γ-linolenic acid.

In various aspects, method utilizes a fatty acid and/or cholesterol that is formulated in a mixture that improves delivery to and/or uptake in cells. In various aspects, the fatty acid and/or cholesterol is associated with a polymer. In various aspects, the fatty acid and/or cholesterol is associated with a protein and/or a synthetic polymer. In various aspects, the fatty acid and/or cholesterol is associated with a small molecule. In various aspects, the fatty acid and/or cholesterol is associated with cyclodextrin.

In various aspects, the method utilizes a scavenging compound that is a carbonyl scavenging compound and/or a free radical scavenging compound. The method, in various aspects, utilizes a carbonyl scavenging compound and a free radical scavenging compound. In various aspects, the method utilizes a scavenging compound that is selected from the group consisting of aminoguanidine, alpha-tocopherol, hydralazine, glycosylisovitexin, N-acetyl-cystein, metformin, penicillamine, pyridoxamine, edaravone (EDA), tenilsetam, lipoic acid, 3,3-dimethyl-D-cysteine (DMC), L-3, 3-dimethyl-D-cysteine (L-DMC), N-acetyl-3,3-dimethyl-D-cysteine (ADMC), $N^{\alpha}$-acetyl-L-cysteine (NAC), 3,3-dimethyl-D-cysteine-disulfide (DMCSS), S-methyl-DMC (SMDMC), L-cysteine (CYS), L-cysteine-O-methylester (CYSM), 3,3-dimethyl-D-cysteine-methylester (DMCM), 3-methyl-3-ethyl-D-cysteine (MEC), semicarbazide hydrochloride SC (hydrazine carboxamide), 1,1-dimethyl-biguanide hydrochloride (DMBG), N-tertbutylhydroxylamine (BHA), a flavonoid, a flavanol, epicatechin, a flavanone, naringenin, a flavonol, quercetin, a flavones, luteolin, an isoflavone, genistein, an anthocyanidin, cyanidin, a phenol/phenolic acid, a flavan-3-ol compound, procyanidins B1 (9.8), procyanidins B2, (+)-catechin, (−)-epicatechin, caftaric acid, caffeic acid, and kaempferol.

In various aspects, the method utilizes a fatty acid that is present at a concentration of at least 5 µM, at least 10 µM, at least 15 µM, at least 20 µM, at least 25 µM, at least 30 µM, at least 35 µM, at least 40 µM, at least 45 µM, at least 50 µM, at least 55 µM, at least 60 µM, at least 65 µM, at least 70 µM, at least 75 µM, at least 80 µM, at least 85 µM, at least 90 µM, at least 95 µM, at least 100 µM, at least 110 µM, at least 120 µM, at least 130 µM, at least 140 µM, at least 150 µm or more, and wherein the fatty acid is present at a concentration of 500 µM or less, or at a concentration that is not toxic to the host cell. Aspects of the methods include use of a fatty acid in a range of about 1 µM to about 100 µM, about 5 µM to about 100 µM, about 5 µM to about 90 µM, about 5 µM to about 85, about 5 µM to about 80 µM, about 5 µM to about 75 µM, about 5 µM to about 70 µM, about 5 µM to about 65 µM, about 5 µM to 60 about µM, about 5 µM to about 55 µM, or about 5 µM to about 50 µM. Aspects of the methods also include use of a fatty acid in a range of about 1 µM to about 100 µM, about 5 µM to about 100 µM, about 10 µM to about 100 µM, about 15 µM to about 100 µM, about 20 µM to about 100 µM, about 25 µM to about 100 µM, about 30 µM to about 100 µM, about 35 µM to about 100 μM, about 40 μM to 100 about μM, about 45 μM to about 100 μM, or about 50 μM to about 100 μM. Aspects of the methods also include use of a fatty acid in a range of about 1 μM to about 100 μM, about 5 μM to about 95 μM, about 10 μM to about 90 μM, about 15 μM to about 85 μM, about 20 μM to about 80 μM, about 25 μM to about 75 μM, about 30 μM to about 70 μM, about 35 μM to about 65 μM, about 40 μM to 60 about μM, or about 45 μM to about 55 μM.

In various aspects, the method utilizes cholesterol that is present at a concentration of at least 5 μM, at least 10 μM, at least 15 μM, at least 20 μM, at least 25 μM, at least 30 μM, at least 35 μM, at least 40 μM, at least 45 μM, at least 50 μM, at least 55 μM, at least 60 μM, at least 65 μM, at least 70 μM, at least 75 μM, at least 80 μM, at least 85 μM, at least 90 μM, at least 95 μM, at least 100 μM, at least 110 μM, at least 120 μM, at least 130 μM, at least 140 μM, at least 150 μM or more and wherein cholesterol is present at a concentration of 500 μM or less, or at a concentration that is not toxic to the host cell. In various aspects, the cholesterol is present at a concentration of less than 450 μM, 400 μM, 350 μM 300 μM, 250 μM, 200 μM or 150 μM. Aspects of the methods include use of cholesterol in a range of about 1 μM to about 100 μM, about 5 μM to about 100 μM, about 5 μM to about 90 μM, about 5 μM to about 85 μM, about 5 μM to about 80 μM, about 5 μM to about 75 μM, about 5 μM to about 70 μM, about 5 μM to about 65 μM, about 5 μM to 60 about μM, about 5 μM to about 55 μM, or about 5 μM to about 50 μM. Aspects of the methods also include use of cholesterol in a range of about 1 μM to about 100 μM, about 5 μM to about 100 μM, about 10 μM to about 100 μM, about 15 μM to about 100 μM, about 20 μM to about 100 μM, about 25 μM to about 100 μM, about 30 μM to about 100 μM, about 35 μM to about 100 μM, about 40 μM to 100 about μM, about 45 μM to about 100 μM, or about 50 μM to about 100 μM. Aspects of the methods also include use of cholesterol in a range of about 1 μM to about 100 μM, about 5 μM to about 95 μM, about 10 μM to about 90 μM, about 15 μM to about 85 μM, about 20 μM to about 80 μM, about 25 μM to about 75 μM, about 30 μM to about 70 μM, about 35 μM to about 65 μM, about 40 μM to 60 about μM, or about 45 μM to about 55 μM.

In various aspects, the method utilizes a scavenging compound that is present at a concentration at least 5 μM, at least 10 μM, at least 15 μM, at least 20 μM, at least 25 μM, at least 30 μM, at least 35 μM, at least 40 μM, at least 45 μM, at least 50 μM, at least 55 μM, at least 60 μM, at least 65 μM, at least 70 μM, at least 75 μM, at least 80 μM, at least 85 μM, at least 90 μM, at least 95 μM, at least 100 μM, at least 110 μM, at least 120 μM, at least 130 μM, at least 140 μM, at least 150 μM or more, and wherein the scavenging compound is present at a concentration of 500 μM or less, or at a concentration that is not toxic to the host cell. In various aspects, the scavenger compound is present at a concentration of less than 10 mM, 9 mM, 8 mM, 7 mM, 6 mM, 5 mM, 4 mM, 3 mM, 2 mM, 1 mM, 950 μM, 900 μM, 850 μM, 800 μM, 750 μM, 700 μM 650 μM, 600 μM, 550 μM, 500 μM 450 μM, 400 μM, 350 μM 300 μM, 250 μM, 200 μM or 150 μM. Aspects of the method include use of a scavenger compound in a range of about 1 μM to about 10 mM, about 1 μM to about 9 mM, about 1 μM to about 8 mM, about 1 μM to about 7 mM, about 1 μM to about 6 mM, about 1 μM to about 5 mM, about 1 μM to about 4 mM, about 1 μM to about 3 mM, about 1 μM to about 2 mM, about 1 μM to about 1 mM, about 1 μM to about 950 μM, about 1 μM to about 900 μM, about 1 μM to about 850 μM, about 1 μM to about 800 μM, about 1 μM to about 750 μM, about 1 μM to about 700 μM, about 1 μM to about 650 μM, about 1 μM to about 600 μM, about 1 μM to about 550 μM, about 1 μM to about 500 μM, about 1 μM to about 450 μM, about 1 μM to about 400 μM, about 1 μM to about 350 μM, about 1 μM to about 300 μM, about 1 μM to about 250 μM, about 1 μM to about 200 μM about 1 μM to about 150 μM, about 1 μM to about 100 μM, about 1 μM to about 95 μM, about 1 μM to about 90 μM, about 1 μM to about 85 μM, about 1 μM to about 80 μM, about 1 μM to about 75 μM, about 1 μM to about 70 μM, about 1 μM to about 65 μM, about 1 μM to about 60 μM, about 1 μM to about 55 μM, about 1 μM to about 50 μM, about 1 μM to about 45 μM, about 1 μM to about 40 μM, about 1 μM to about 35 μM, about 1 μM to about 30 μM, about 1 μM to about 25 μM, about 1 μM to about 20 μM, about 1 μM to about 15 μM, or about 1 μM to about 10 μM. Aspects of the method also include use of a scavenger compound in a range of about 1 μM to about 10 mM, about 10 μM to about 10 mM, about 20 μM to about 10 mM, about 30 μM to about 10 mM, about 40 μM to about 10 mM, about 50 μM to about 10 mM, about 60 μM to about 10 mM, about 70 μM to about 10 mM, about 80 μM to about 10 mM, about 90 μM to about 10 mM, about 100 μM to about 10 mM, about 150 μM to about 10 mM, about 200 μM to about 10 mM, about 250 μM to about 10 mM, about 300 μM to about 10 mM, about 350 μM to about 10 mM, about 400 μM to about 10 mM, about 450 μM to about 10 mM, about 500 μM to about 10 mM, about 550 μM to about 10 mM, about 600 μM to about 10 mM, about 650 μM to about 10 mM, about 700 μM to about 10 mM, about 750 μM to about 10 mM, about 800 μM to about 10 mM, about 850 μM to about 10 mM about 900 μM to about 10 mM, about 1 mM to about 10 mM, about 2 mM to about 10 mM, about 3 mM to about 10 mM, about 4 mM to about 10 mM, about 5 mM to about 10 mM, about 6 mM to about 10 mM, about 8 mM to about 10 mM, or about 9 mM to about 10 mM. Aspects of the method also include use of a scavenger compound in a range of about 1 μM to about 10 mM, about 10 μM to about 1 mM, about 50 μM to about 950 μM, about 100 μM to about 900 μM, about 150 μM to about 850 μM, about 200 μM to about 800 μM, about 250 μM to about 750 μM, about 300 μM to about 700 μM, about 350 μM to about 650 μM, about 400 μM to about 600 μM, about 450 μM to about 550 μM, or about 400 μM to about 500 μM.

In various aspects, the method utilizes a fatty acid that is present at a concentration of no more than 5 μM, no more than 10 μM, no more than 15 μM, no more than 20 μM, no more than 25 μM, no more than 30 μM, no more than 35 μM, no more than 40 μM, no more than 45 μM, no more than 50 μM, no more than 55 μM, no more than 60 μM, no more than 65 μM, no more than 70 μM, no more than 75 μM, no more than 80 μM, no more than 85 μM, no more than 90 μM, no more than 95 μM, no more than 100 μM, no more than 110 μM, no more than 120 μM, no more than 130 μM, no more than 140 μM, no more than 150 μM.

In various aspects, the method utilizes cholesterol that is present at a concentration of no more than 5 μM, no more than 10 μM, no more than 15 μM, no more than 20 μM, no more than 25 μM, no more than 30 μM, no more than 35 μM, no more than 40 μM, no more than 45 μM, no more than 50 μM, no more than 55 μM, no more than 60 μM, no more than 65 μM, no more than 70 μM, no more than 75 μM, no more than 80 μM, no more than 85 μM, no more than 90 μM, no more than 95 μM, no more than 100 μM, no more than 110 μM, no more than 120 μM, no more than 130 μM, no more than 140 μM, no more than 150 μM.

In various aspects, the method utilizes a scavenging compound that is present at a concentration of no more than 5 μM, no more than 10 μM, no more than 15 μM, no more than 20 μM, no more than 25 μM, no more than 30 μM, no more than 35 μM, no more than 40 μM, no more than 45 μM, no more than 50 μM, no more than 55 μM, no more than 60 μM, no more than 65 μM, no more than 70 μM, no more than 75 μM, no more than 80 μM, no more than 85 μM, no more than 90 μM, no more than 95 μM, no more than 100 μM, no more than 110 μM, no more than 120 μM, no more than 130 μM, no more than 140 μM, no more than 150 μM.

Additional aspects and details of the invention will be apparent from the following examples, which are intended to be illustrative rather than limiting.

EXAMPLES

Example 1

The possibility that the yield of HCMV could be improved was tested by adding specific fatty acids to the medium of infected human MRC5 fibroblasts (American Type Culture Collection).

Cells were infected with the AD169 strain of HCMV at a multiplicity of 0.5 infectious units/cell, and immediately following a 2-hour adsorption period, cells were fed with medium (Dulbecco's Modified Eagle Medium, DMEM) containing 10% fetal calf serum plus various fatty acids, cholesterol and carbonyl scavenging compound. At 96 hours post infection, infectious virus in the medium was assayed by fluorescent focus assay using antibody to the HCMV IE1 protein.

Briefly, About 90% confluent MRC5 human fibroblasts were infected with HCMV at a multiplicity of 0.5 IU/cell. Two hours after infection, medium was replaced with fresh medium containing 10% fetal calf serum and either of oleic acid (OA, up to about 100 μM), linoliec acid (LA, up to about 100 μM), α-linolenic acid (LLA, up to about 100 μM), eicosapentaenoic acid (EPA, up to about 75 μM), or docosahexaenoic acid (DHA, up to about 50 μM). The experiment was also performed in the presence of either aminoguanidine (AG, up to about 250 μM) or cholesterol (chol., up to about 13 μM). Virus production at 96 hours after infection was determined by fluorescent focus assay in MRC-5 cells and shown as a fold change relative to no treatment (NT) which was $5 \times 10^5$ infectious units. The fold-changes are the average of two independent infections. Results are shown in FIG. 1.

As is evident in FIG. 1, oleic acid (OA) reduced the yield of HCMV; linoleic acid (LA) had little effect on the yield; and α-linolenic acid (LLA) increased the yield by about 1.2-fold. Eicosapentaenoic acid (EPA) and docosahexaenoic acid (DHA) increased HCMV yield by factors of 2.5 and 4.6, respectively. Further, although aminoguanidine alone increased the yield of HCMV by a factor of about 2.6, the increase resulting from addition of the carbonyl scavenging compound was reduced by inclusion of OA, LA or LLA. In contrast, aminoguanidine plus EPA gave a slightly higher yield than either additive alone, and the combination of aminoguanidine plus DHA increased the yield by a factor of 6.2, a substantially higher yield than achieved with no additive or either additive alone. Addition of cholesterol alone (cholesterol solution, Sigma Aldrich #S5442) had no effect on HCMV yield and it did not improve, and in some cases inhibited, the enhancing effects of fatty acids. These results show that the addition of fatty acids can enhance the yield of HCMV obtained from cultured MRC5 fibroblasts, and this enhancement can be further increased by inclusion of a carbonyl scavenging compound.

Example 2

Experiments along the line of those conducted in Example 1 were designed to determine whether the addition of other fatty acids or fatty acid derivatives, (e.g., arachidonic acid (AA) or its derivatives) alone or in combination with cholesterol or cholesterol derivatives, with or without aminoguanidine or another carbonyl scavenging compound or a free radical scavenging compound, could enhance the yield of HCMV.

Briefly, about 90% confluent MRC5 fibroblasts were infected with HCMV at a multiplicity of 0.5 IU/cell. Two hours after infection, medium was replaced with fresh medium containing 10% fetal calf serum and α-tocopherol (α-T) or aminoguanidine (AG) at indicated concentrations. Virus production at 96 h after infection was determined by fluorescent focus assay in which MRC-5 cells and shown as a fold change relative to no treatment (NT). The fold-changes are the average of two independent infections. Results are set out in FIG. 2.

Figure 2:
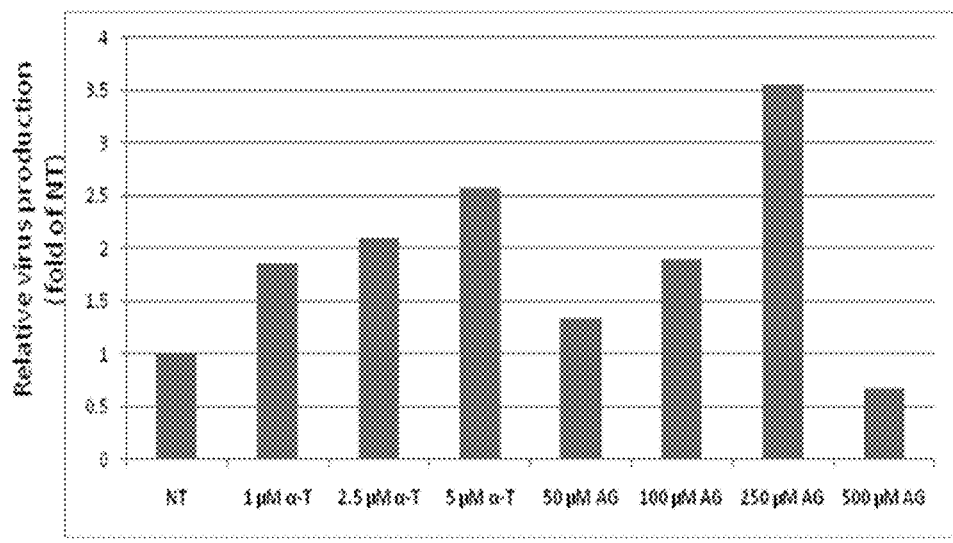
FIG. 2. The effect of carbonyl/free radical scavenging compounds on HCMV yields.

This enhancement could be observed in MRC5 fibroblasts, other fibroblasts or other cell types suitable for the growth of HCMV. To the extent that the alternative fatty acid, cholesterol, carbonyl scavenging compounds and cell types enhance the production of HCMV, this invention encompasses their use in the process of virus growth. FIG. 2 shows an example of second carbonyl scavenging compound/free radical scavenging compound, alpha-tocopherol (αT), which enhances the production of HCMV as observed for aminoguanidine.

Further, certain formulations of natural or artificial fatty acids, which can be elongated and/or unsaturated within cells to produce AA or DHA, respectively, are used to substitute for AA or DHA.

An exemplary, but not limiting, embodiment of this invention includes supplementation of medium supporting MRC5 cells with docosahexaenoic acid (DHA), a dietary-essential omega-3 polyunsaturated fatty acid (PUFA), plus aminoguanidine, a carbonyl scavenging compound.

Example 3

The possibility was tested that the yield of VZV also could be improved by adding specific fatty acids to the medium of infected human MRC5 fibroblasts.

For this test, MRC5 cells (passage 20-25) were seeded at a density of 300.000 cell/100 mm culture dish and grown in 15 ml of DMEM containing 10% fetal calf serum plus 2 mM glutamax (Invitrogen) at 35° C. A lipid mixture (LM-1, 1 ml/liter medium, Sigma Aldrich #L5146) was added to the cells either at the time of seeding or 1 day after seeding. Three days later, the culture medium was replaced with 10 ml growth medium containing 50 mM sucrose as a stabilizer. The cells were further incubated for 3 days and growth medium was replaced with fresh medium containing no sucrose. After cells reached confluence, they were infected with VZV by adding infected cells (1 infected cell/50 uninfected cells; infected cells were from a preparation frozen in a solution of 10% DMSO plus 90% fetal calf serum and stored in liquid nitrogen). At the time of infection, the cultures were re-fed with DMEM containing 10% fetal calf serum plus 2 mM glutamax. Arachidonic acid (AA)+alpha-tocopherol (αT) or DHA+αT were added at the indicated times. 72 hours after infection, cells were washed twice with PBS, and incubated in 10 ml of PBS containing 50 mM ammonium chloride for 50 minutes at 4° C. The cells were harvested and frozen in PSGC buffer (Harper et al., *Arch Virol* 143:1163-70, 1998) at −80° C. Infectious virus was subsequently quantified by plaque assay of sonicated cells on ARPE-19 cells (American Type Culture Collection). Results are set out in FIG. 3.

Results indicates that addition of LM-1 during cell growth prior to infection enhanced the virus yield by a factor of nearly two, but addition at 1 day after infection did not enhance virus production. However, addition of AA+αT or DHA+αT at various times after infection enhanced the production of infectious virus, with the greatest enhancement of virus yield occurring when the fatty acid and carbonyl scavenging compound were added between 1-6 hours post infection.

Figure 4:
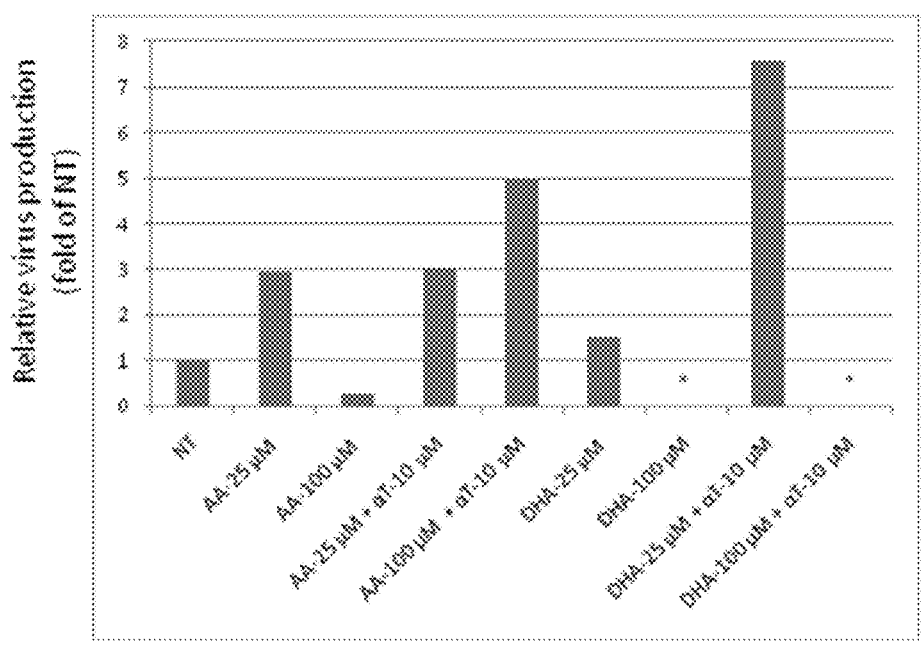
FIG. 4. αT enhances the ability of AA and DHA to facilitate VZV replication.

The experiment was repeated, varying the amount of fatty acid and αT added to MRC5 cells at 6 hours post infection and the results are set out in FIG. 4.

Briefly, in these repeat experiments, MRC5 cells were infected with VZV at an MOI=1:50. AA, DHA, and αT were added to the cells at 6 hpi as indicated. 72 hours after infection, the cells were harvested into PSGC buffer and frozen at −80° C. for later processing. After thawing, the cells were sonicated and the yield of cell free VZV quantified by standard plaque assay on ARPE-19 cells. Fold change relative to no treatment (NT) is shown. (*) indicates that the composition produced cytotoxicity that was evident upon visual inspection. The fold-changes are the average of two independent infections.

As shown in FIG. 4, in the absence of the carbonyl scavenging agent, 25 μM AA enhanced the yield of virus, whereas 100 μM AA inhibited virus production; in contrast, in the presence of αT, both doses of AA increased the virus yield, with 100 μM showing the greatest increase at 5 fold. Similarly, 25 μM DHA alone increased the yield by a factor of about 1.5, whereas 25 μM DHA+αT produced a 7.5-fold increase. 100 μM DHA was toxic in the absence or presence of αT.

These experiments demonstrate that the addition of certain fatty acids together with a carbonyl scavenging agent after infection with VZV augment the production of infectious progeny. The addition of the non-essential fatty acid, oleic acid (100 μM), reduced VZV production by a factor of 2, without causing observable cellular toxicity.

Example 4

Figure 3:
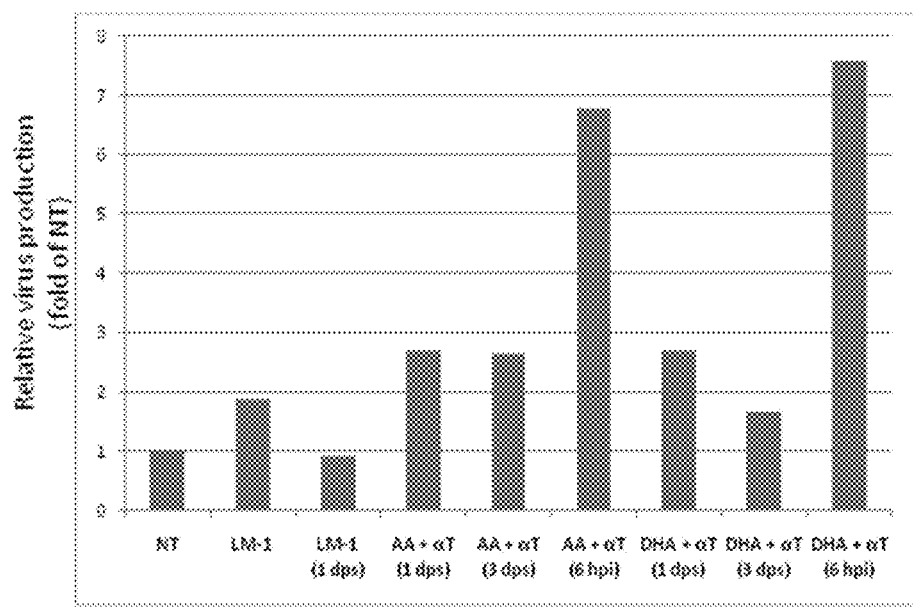
FIG. 3. The effect of supplementing the cells with AA or DHA on VZV yields.

In the experiments presented in FIGS. 3 and 4, the infected cells were harvested into PSGC buffer, frozen, subsequently thawed and disrupted by sonication and then titered. Next the yield of infectious virus obtained by this method was compared to an alternative method where infected cells were harvested into PSGC buffer, immediately disrupted by sonication, and then frozen at −80° C. prior to titration.

Figure 5:
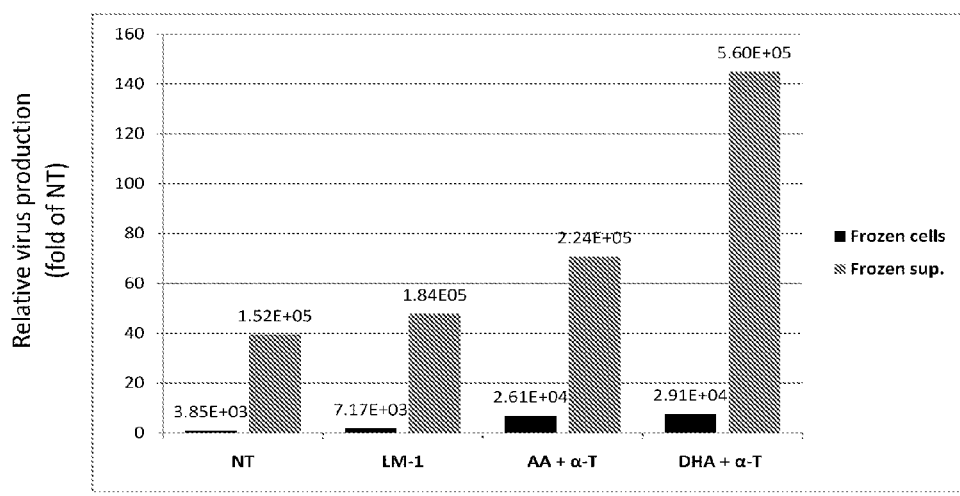
FIG. 5. The effect of different processing methods on VZV yield.
Figure 6:
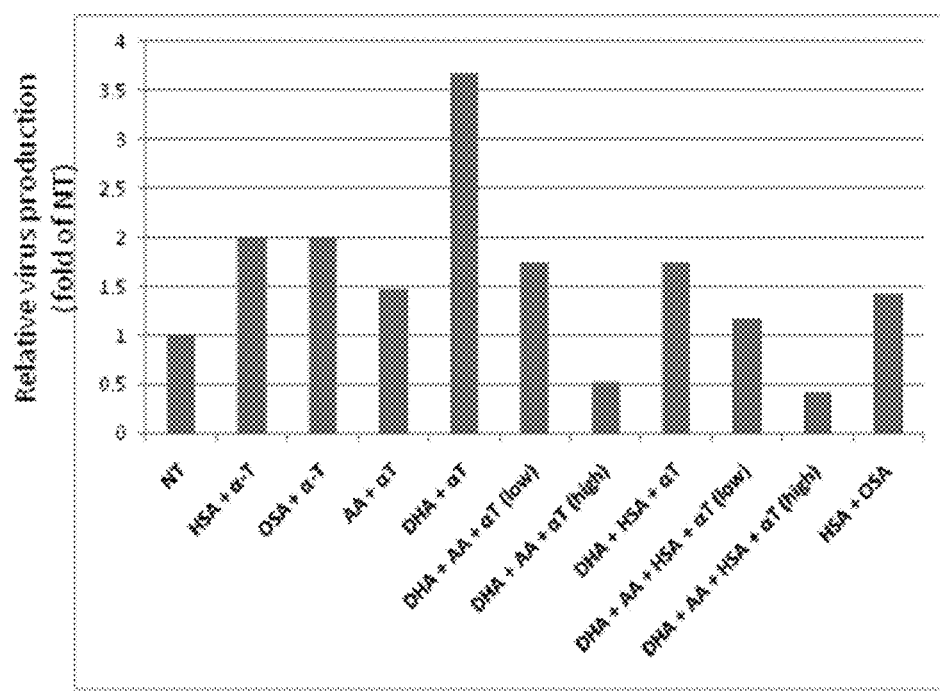
FIG. 6. The effect of supplementing the cells with different combinations of fatty acids on VZV yield.

In brief, MRC5 cells were infected with VZV at an M0I=1:50. Lipid mixture 1(LM-1) was added to the cells immediately after cell seeding. At 6 hours after infection, up to about 100 μM AA or 25 up to about μM DHA was added to cells together with up to about 10 μM αT. 72 hours after infection, the cells were harvested into PSGC buffer and either frozen at −80° C. and sonicated later for the release of virus (frozen cells) or immediately sonicated after harvesting and supernatants containing the cell-free VZV were frozen at −80° C. (frozen sup.) prior to titration. Cell-free VZV yield was quantified by plaque assay on APRE-19 cells. Fold change relative to no treatment (NT) is shown. The numbers above the bars indicate the amount of virus obtained per ml in the corresponding treatment. The results are set out in FIG. 5.

Example 5

Having improved the yield of infectious VZV by sonicating infected cells in PSGC buffer before freezing, tested the effect of additional fatty acids (hexacosanoic acid (HSA), and octacosanoic acid (OSA) and fatty acid combinations on virus production was tested. Results are set out in FIG. 6.

Although HSA and OSA improved virus yields in comparison to no treatment, these additional fatty acids and combinations did not perform as well as DHA+αT. Further, high doses of two combinations generated less virus than no treatment, presumably due to toxicity resulting from high total concentrations of the combined fatty acids.

Briefly, MRC5 cells were infected with VZV at an MOI=1:50. Six hours after infection cells were treated with indicated combinations of lipids plus 10 μM αT. Hexacosanoic acid (HSA) and octacosanoic acid (OSA) were dissolved in 20 mg/ml α-cyclodextin (Sigma-Aldrich) in PBS by sonication and added to a solution of 10 mg/ml fatty acid-free BSA (Sigma-Aldrich) in PBS (1:1, v/v) to give a stock concentration of 10 mM for each fatty acid. HSA, OSA, and DHA were used at 25 μM, and AA was used at 25 μM. Two sets of fatty acid concentrations was used for combination treatments: DHA, AA, and HSA was either added at concentrations of 25 μM, 100 μM, and 25 μM (high), or 10 μM, 50 μM, and 10 μM (low), respectively. 72 hours after infection, the cells were harvested into PSGC buffer, sonicated immediately and the yield of cell free VZV quantified by plaque assay on ARPE-19 cells. Fold change relative to no treatment (NT) is shown. The fold-changes are the average of two independent infections. Results are shown in FIG. 6.

It is possible that the relatively poor performance of HSA and OSA in the experiment presented in FIG. 5 resulted from difficulty in achieving efficient delivery of the fatty acids to cells. Alternative formulations of the fatty acids are contemplated to improve uptake and stimulate more efficient virus production.

Example 6

Next the possibility that the addition of cholesterol would further enhance the elevated yields obtained by supplementation with fatty acids was tested.

MRC5 cells were infected at a MOI of 1:100, and harvested either at 48 or 72 hours after infection. As controls, the cells were treated with two different mixtures of lipids immediately after cell seeding. LM-1 is rich in omega-3 fatty acids, and LM-2 (Invitrogen, #11905) is a chemically defined mixture that contains mainly omega-6 fatty acids.

Briefly, MRC5 cells were grown in DMEM containing 10% fetal calf serum, 2 mM glutamax (Invitrogen) at 35° C. as described in the text. Lipid mixture 1 (LM-1, Sigma) or 2 (LM-2, Invitrogen) was added to the cells immediately after seeding. The cells were infected with VZV at an MOI=1:100. Six hours after infection cells were treated with indicated lipid combinations plus 10 μM αT. HSA and DHA were used at 25 μM, and AA was used at 100 μM. Where indicated, 13 μM cholesterol was added on the cells. 48 or 72 hours after infection, the cells were harvested into PSGC buffer, sonicated immediately and the yield of cell free VZV quantitated by standard plaque assay on ARPE-19 cells. Fold change relative to no treatment (NT) harvested at 48 hpi is shown. The numbers above the bars indicate the amount of virus obtained per ml in the corresponding treatment. The fold-changes are the average of two independent infections. Results are set out in FIG. 7.

Both lipid mixtures slightly and similarly elevated VZV yields at both times. The effects of these lipid mixtures were not as large as the effects of the individual fatty acids. DHA, AA and HSA were tested with α-T, and, as in previous experiments, each of these additives elevated the yield of VZV at 72 hours post infection. Cholesterol was also tested as a supplement and at 72 hr after infection, it increased the yield of VZV by a factor of about two relative to no treatment. Yields were much lower at 48 than at 72 hours after infection. Finally, the effect of cholesterol addition to DHA+α-T and DHA+HSA+ α-T was tested, and it proved to further increase the yield of VZV. At 72 hours post infection, $9.6 \times 10^5$ PFU/ml of infectious VZV was achieved by supplementation with DHA+α-T plus cholesterol.

Example 7

The yield of virus particles by quantifying the amount of viral DNA in virus stocks by using quantitative PCR (qPCR) was then quantified.

Virus stocks were treated with DNase I before qPCR analysis. Before DNase I treatment, cellular DNA was detected in virus stocks using primers specific for the actin locus, but after treatment with the enzyme, cellular DNA was no longer detected. This observation demonstrated that the DNase I treatment effectively degraded DNA in the virus stocks that was not protected within virus particles. Each copy of DNase I-resistant VZV DNA was taken as a proxy for one virus particle.

Figure 7:
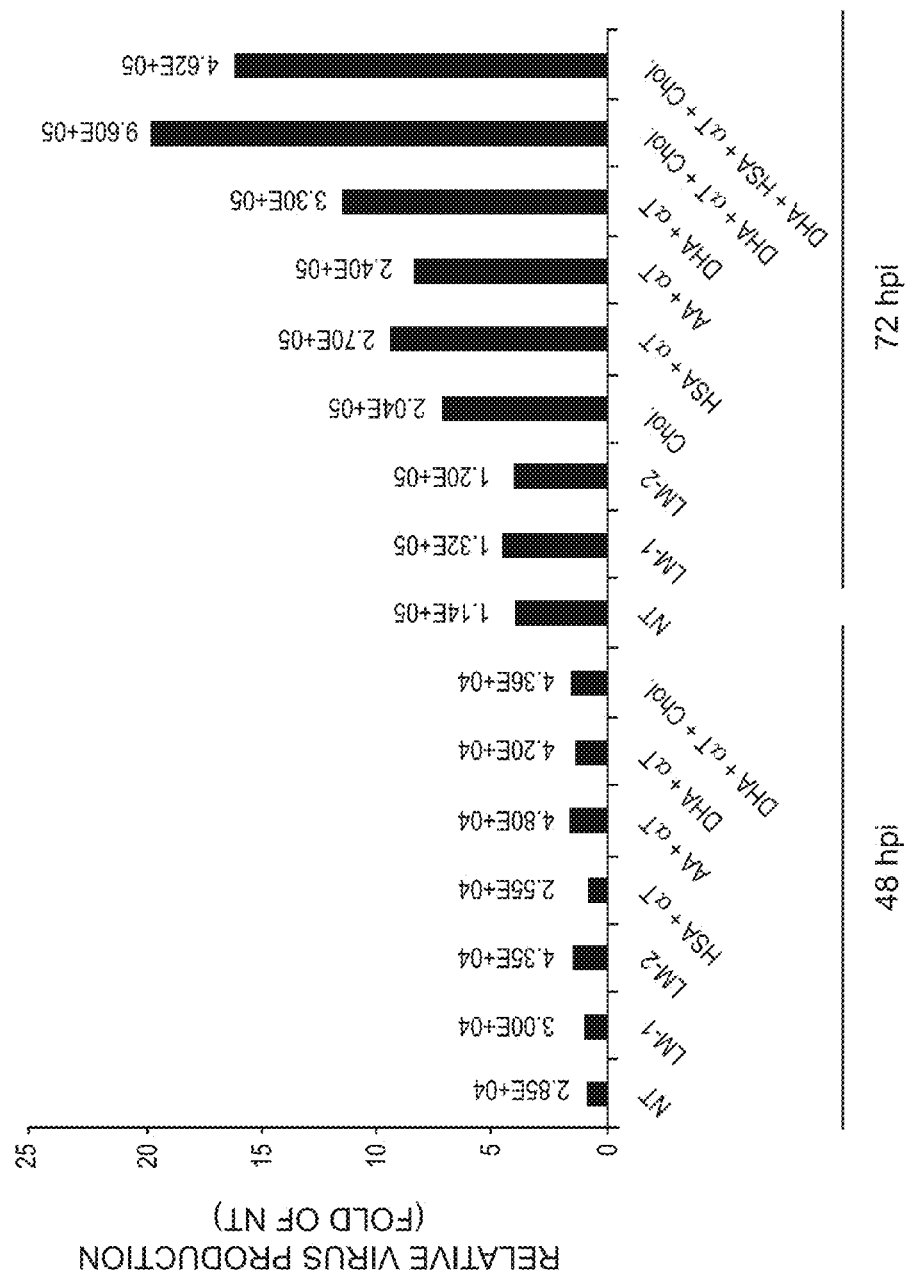
FIG. 7. Cholesterol enhances the ability of DHA to facilitate cell-free VZV production.

Briefly, cell-free VZV was obtained from the cells treated with the indicated combinations of lipid mixture (LM-1, Sigma), DHA (about 25 μM) plus αT (about 10 μM), and cholesterol (about 13 μM), as described in the legend to FIG. 7. The samples were treated with DNAse I (2 units, 30 min, 37° C.) to remove contaminating DNA outside the viral envelope and the number of particles containing viral genome was determined by quantitative real-time PCR analysis. In parallel, the amount of virus produced was determined by plaque assay and infectivity of the viruses was calculated by dividing the number of enveloped virus particles by number of infectious virus produced (particle/PFU). The results are shown as fold change relative to no treatment (NT).

Figure 8:
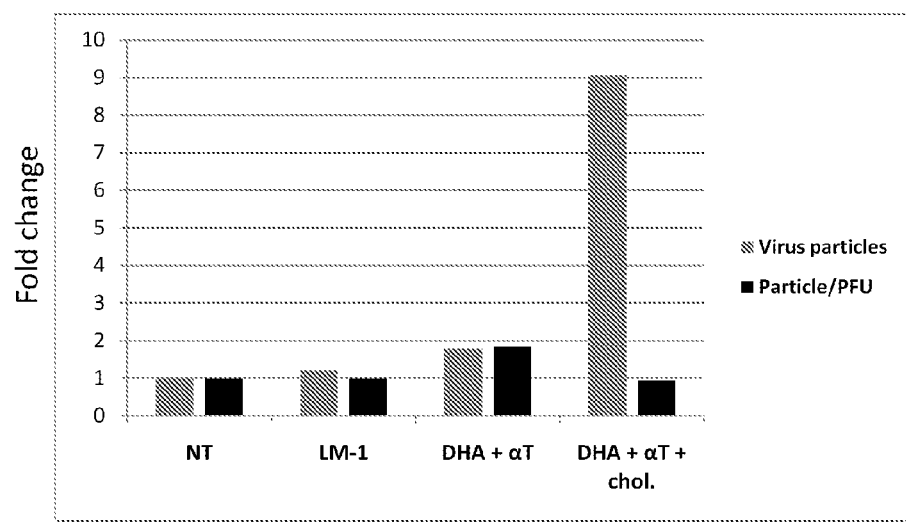
FIG. 8. The effect of DHA plus α-T treatment on virus particle production and infectivity of VZV.

The amount of infectivity in each sample was determined in parallel by plaque assay. As shown in FIG. 8, the number of virus particles and the specific infectivity of the particles were little changed by LM-1 as compared to no treatment. Addition of DHA+αT at 6 hours post infection increased the number of virus particles and also increased the particle/PFU ratio by a factor of nearly 2. Addition of DHA+αT+cholesterol had no effect on the specific infectivity of virus particles (particles/ PFU), but it increased the number of virus particles by a factor of 9.

Importantly, then, addition of DHA+αT+cholesterol at 6 hours post infection increased the yield of virus particles and infectivity by a factor of 9 at 72 hours post infection as compared to no treatment.

Example 8

Figure 9:
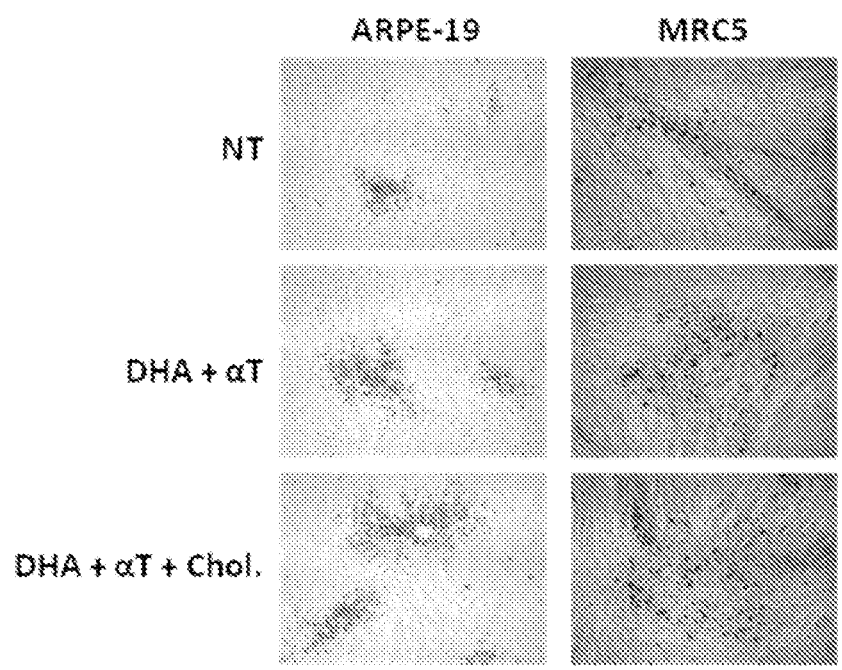
FIG. 9. The spread of VZV in the cells treated with DHA in combination with α-T and cholesterol.

Viral spread was monitored by assaying the size of infected foci at 72 hours post infection (FIG. 9).

Briefly, ARPE-19 and MRC5 cells were infected with VZV at an MOI=1:250. The indicated combinations of DHA (25 μM), αT (10 μM) and cholesterol (chol.; 13 μM) was added to the cells at 6 hpi. The cells were photographed 72 hours after infection. As shown in FIG. 9, foci were larger in cells treated with DHA+αT and larger yet when treated with DHA+αT+ cholesterol, consistent with the view that the treatments accelerated virus spread from cell to cell.

Numerous modifications and variations in the invention as set forth in the above illustrative examples are expected to occur to those skilled in the art. Consequently only such limitations as appear in the appended claims should be placed on the invention.

What is claimed is:

1. A method for producing a virus comprising:
culturing a host cell infected with a virus under conditions appropriate for producing the virus, wherein:
the conditions include post-infection addition of supplemental fatty acid of at least 20 carbon atoms and a carbonyl and/or a free radical scavenging compound in amounts and for a time effective to improve the amount of virus production compared to virus produced in the method performed without the supplemental fatty acid and scavenger compound.

2. The method of claim 1, wherein the fatty acid is selected from the group consisting of eicosapentaenoic acid (EPA), docosahexaenoic acid (DHA), arachidonic acid (AA), hexacosanoic acid (HSA) and octacosanoic acid, OSA).

3. The method of claim 1, wherein:
the addition further includes cholesterol, and
the virus is produced in an amount greater in the presence of the supplemental fatty acid, scavenger and cholesterol compared to virus produced in the method performed without the supplemental fatty acid, scavenger and cholesterol.

4. The method of claim 2, wherein:
the addition further includes cholesterol, and
the virus is produced in an amount greater in the presence of the supplemental fatty acid, scavenger and cholesterol compared to virus produced in the method performed without the supplemental fatty acid, scavenger and cholesterol.

5. The method of claim 1, wherein the carbonyl and/or a free radical scavenging compound is selected from the group consisting of aminoguanidine, alpha-tocopherol, hydralazine, glycosylisovitexin, N-acetyl-cystein, metformin, penicillamine, pyridoxamine, edaravone (EDA), tenilsetam, lipoic acid, 3,3-dimethyl-D-cysteine (DMC), L-3,3-dimethyl-D-cysteine (L-DMC), N-acetyl-3,3-dimethyl-D-cysteine (ADMC), Nα-acetyl-L-cysteine (NAC), 3,3-dimethyl-D-cysteine-disulfide (DMCSS), S-methyl-DMC (SMDMC), L-cysteine (CYS), L-cysteine-O-methylester (CYSM), 3,3-dimethyl-D-cysteine-methylester (DMCM), 3-methyl-3-ethyl-D-cysteine (MEC), semicarbazide hydrochloride SC (hydrazine carboxamide), 1,1-dimethyl-biguanide hydrochloride (DMBG), N-tertbutylhydroxylamine(BHA), a flavonoid, a flavanol, epicatechin, a flavanone, naringenin, a flavonol, quercetin, a flavones, luteolin, an isoflavone, genistein, an anthocyanidin, cyanidin, a phenol/phenolic acid, a flavan-3-ol compound, procyanidins B1 (9.8), procyanidins B2, (+)-catechin, (−)-epicatechin, caftaric acid, caffeic acid, and kaempferol.

6. The method of claim 5, wherein the carbonyl and/or a free radical scavenging compound is aminoguanidine or alpha-tocopherol.

7. The method of claim 2, wherein the scavenging compound is selected from the group consisting of aminoguanidine, alpha-tocopherol, hydralazine, glycosylisovitexin, N-acetyl-cystein, metformin, penicillamine, pyridoxamine, edaravone (EDA), tenilsetam, lipoic acid, 3,3-dimethyl-D-cysteine (DMC), L-3,3-dimethyl-D-cysteine (L-DMC), N-acetyl-3,3-dimethyl-D-cysteine (ADMC), Nα-acetyl-L-cysteine (NAC), 3,3-dimethyl-D-cysteine-disulfide (DMCSS), S-methyl-DMC (SMDMC), L-cysteine (CYS), L-cysteine-O-methylester (CYSM), 3,3-dimethyl-D-cysteine-methylester (DMCM), 3-methyl-3-ethyl-D-cysteine (MEC), semicarbazide hydrochloride SC (hydrazine carboxamide), 1,1-dimethyl-biguanide hydrochloride (DMBG), N-tertbutylhydroxylamine(BHA), a flavonoid, a flavanol, epicatechin, a flavanone, naringenin, a flavonol, quercetin, a flavones, luteolin, an isoflavone, genistein, an anthocyanidin, cyanidin, a phenol/phenolic acid, a flavan-3-ol compound, procyanidins B1 (9.8), procyanidins B2, (+)-catechin, (−)-epicatechin, caftaric acid, caffeic acid, and kaempferol.

8. The method of claim 7, wherein the scavenging compound is aminoguanidine or alpha-tocopherol.

9. The method of claim 3, wherein the carbonyl and/or a free radical scavenging compound is selected from the group consisting of aminoguanidine, alpha-tocopherol, hydralazine, glycosylisovitexin, N-acetyl-cystein, metformin, penicillamine, pyridoxamine, edaravone (EDA), tenilsetam, lipoic acid, 3,3-dimethyl-D-cysteine (DMC), L-3,3-dimethyl-D-cysteine (L-DMC), N-acetyl-3,3-dimethyl-D-cysteine (ADMC), Nα-acetyl-L-cysteine (NAC), 3,3-dimethyl-D-cysteine-disulfide (DMCSS), S-methyl-DMC (SMDMC), L-cysteine (CYS), L-cysteine-O-methylester (CYSM), 3,3-dimethyl-D-cysteine-methylester (DMCM), 3-methyl-3-ethyl-D-cysteine (MEC), semicarbazide hydrochloride SC (hydrazine carboxamide), 1,1-dimethyl-biguanide hydrochloride (DMBG), N-tertbutylhydroxylamine(BHA), a flavonoid, a flavanol, epicatechin, a flavanone, naringenin, a flavonol, quercetin, a flavones, luteolin, an isoflavone, genistein, an anthocyanidin, cyanidin, a phenol/phenolic acid, a flavan-3-ol compound, procyanidins B1 (9.8), procyanidins B2, (+)-catechin, (−)-epicatechin, caftaric acid, caffeic acid, and kaempferol.

10. The method of claim 9, wherein the carbonyl and/or a free radical scavenging compound is aminoguanidine or alpha-tocopherol.

* * * * *